(12) United States Patent
Langedijk

(10) Patent No.: US 10,953,087 B2
(45) Date of Patent: Mar. 23, 2021

(54) STABILIZED PRE-FUSION RSV F PROTEINS

(71) Applicant: Janssen Vaccines & Prevention B.V., Leiden (NL)

(72) Inventor: Johannes Petrus Maria Langedijk, Amsterdam (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 56 days.

(21) Appl. No.: 16/305,169

(22) PCT Filed: May 29, 2017

(86) PCT No.: PCT/EP2017/062875
§ 371 (c)(1),
(2) Date: Nov. 28, 2018

(87) PCT Pub. No.: WO2017/207480
PCT Pub. Date: Dec. 7, 2017

(65) Prior Publication Data
US 2020/0138940 A1    May 7, 2020

(30) Foreign Application Priority Data
May 30, 2016 (EP) .................................. 16172008

(51) Int. Cl.
| A61K 39/00 | (2006.01) |
| C07K 14/005 | (2006.01) |
| A61K 39/155 | (2006.01) |
| C07K 16/10 | (2006.01) |
| C12N 7/00 | (2006.01) |
| C07K 14/135 | (2006.01) |

(52) U.S. Cl.
CPC .......... A61K 39/155 (2013.01); C07K 14/135 (2013.01); C12N 7/00 (2013.01); *C07K 2317/565* (2013.01); *C12N 2760/18522* (2013.01); *C12N 2760/18534* (2013.01)

(58) Field of Classification Search
CPC .......... A61P 31/14; C12N 2760/18534; C07K 14/005; A61K 39/155; A61K 39/12
See application file for complete search history.

(56) References Cited

U.S. PATENT DOCUMENTS

| 4,235,877 | A | 11/1980 | Fullerton |
| 4,372,945 | A | 2/1983 | Likhite |
| 4,474,757 | A | 10/1984 | Amon et al. |
| 5,057,540 | A | 10/1991 | Kensil et al. |
| 5,122,458 | A | 6/1992 | Post et al. |
| 5,385,839 | A | 1/1995 | Stinski |
| 5,559,099 | A | 9/1996 | Wickham et al. |
| 5,837,511 | A | 11/1998 | Falck-Pedersen et al. |
| 5,837,520 | A | 11/1998 | Shabram et al. |
| 5,846,782 | A | 12/1998 | Wickham et al. |
| 5,851,806 | A | 12/1998 | Kovesdi et al. |
| 5,891,690 | A | 4/1999 | Massie |
| 5,965,541 | A | 10/1999 | Wickham et al. |
| 5,981,225 | A | 11/1999 | Kochanek et al. |
| 5,994,106 | A | 11/1999 | Kovesdi et al. |
| 5,994,128 | A | 11/1999 | Fallaux et al. |
| 6,020,191 | A | 2/2000 | Scaria et al. |
| 6,040,174 | A | 3/2000 | Imler et al. |
| 6,083,716 | A | 7/2000 | Wilson et al. |
| 6,113,913 | A | 9/2000 | Brough et al. |
| 6,225,289 | B1 | 5/2001 | Kovesdi et al. |
| 6,261,823 | B1 | 7/2001 | Tang et al. |
| 6,485,958 | B2 | 11/2002 | Blanche et al. |
| 7,270,811 | B2 | 9/2007 | Bout et al. |
| 7,326,555 | B2 | 2/2008 | Konz, Jr. et al. |
| 8,772,256 | B2 | 7/2014 | Graham et al. |
| 8,932,607 | B2 | 1/2015 | Custers et al. |
| 2011/0305727 | A1 | 12/2011 | Swanson et al. |
| 2012/0164176 | A1 | 6/2012 | Swanson et al. |
| 2012/0315270 | A1 | 12/2012 | McLellan et al. |
| 2013/0177573 | A1 | 7/2013 | Williamson et al. |
| 2014/0073032 | A1 | 3/2014 | Custers et al. |
| 2014/0248314 | A1 | 9/2014 | Swanson et al. |
| 2014/0271699 | A1 | 9/2014 | Kwong et al. |
| 2016/0102123 | A1 | 4/2016 | Langedijk et al. |
| 2016/0145321 | A1 | 5/2016 | Wadia et al. |
| 2016/0145322 | A1 | 5/2016 | Wadia et al. |
| 2016/0176932 | A1 | 6/2016 | Langedijk et al. |

FOREIGN PATENT DOCUMENTS

| EP | 0853660 A1 | 7/1998 |
| EP | 1230354 | 8/2002 |
| WO | 90003184 A1 | 4/1990 |
| WO | 9014837 A1 | 12/1990 |
| WO | 96/09378 A1 | 3/1996 |
| WO | 9611711 A1 | 4/1996 |
| WO | 98/22588 A2 | 5/1998 |
| WO | 98/39411 A1 | 9/1998 |
| WO | 99/12568 A1 | 3/1999 |

(Continued)

OTHER PUBLICATIONS

McLellan et al., "Structural Basis of Respiratory Syncytial Virus Neutralization by Motavizumab," Nature Structural & Molecular Biology, vol. 17, pp. 248-250 (2010).

McLellan et al., "Structure of RSV Fusion Glycoprotein Trimer Bound to a Prefusion-Specific Neutralizing Antibody," Science, vol. 340, pp. 1113-1117 (2013).

McLellan et al., "Structure-Based Design of a Fusion Glycoprotein Vaccine for Respiratory Syncytial Virus," Science, vol. 342, pp. 592-598 (2013).

Swanson et al., "Structural Basis for Immunization with Postfusion Respiratory Syncytial Virus Fusion F Glycoprotein (RSV F) to Elicit High Neutralizing Antibody Titers," PNAS, vol. 108, pp. 9619-9624 (2011).

(Continued)

*Primary Examiner* — Barry A Chestnut
(74) *Attorney, Agent, or Firm* — Ice Miller LLP

(57) ABSTRACT

Stable pre-fusion respiratory syncitial virus (RSV) F proteins, immunogenic compositions including the proteins and uses thereof for the prevention and/or treatment of RSV infection are described.

32 Claims, 4 Drawing Sheets

Specification includes a Sequence Listing.

(56) References Cited

FOREIGN PATENT DOCUMENTS

| WO | 99/41416 | A2 | 8/1999 |
|---|---|---|---|
| WO | 2000/29024 | A1 | 5/2000 |
| WO | 2000/32754 | A1 | 6/2000 |
| WO | 2000/70071 | A1 | 11/2000 |
| WO | 2001/66137 | A1 | 9/2001 |
| WO | 2001085984 | A1 | 11/2001 |
| WO | 2002/40665 | A2 | 5/2002 |
| WO | 0304018 | A1 | 5/2003 |
| WO | 2003/049763 | A1 | 6/2003 |
| WO | 2003/061708 | A1 | 7/2003 |
| WO | 2003/078592 | A2 | 9/2003 |
| WO | 2003/104467 | A1 | 12/2003 |
| WO | 2004001032 | A2 | 12/2003 |
| WO | 2004004762 | A1 | 1/2004 |
| WO | 2004/020971 | A2 | 3/2004 |
| WO | 2005002620 | A1 | 1/2005 |
| WO | 2005071093 | A2 | 8/2005 |
| WO | 2005/080556 | A2 | 9/2005 |
| WO | 2006/108707 | A1 | 10/2006 |
| WO | 2007/104792 | A2 | 9/2007 |
| WO | 2007/110409 | A1 | 10/2007 |
| WO | 2009/11713 | A1 | 1/2009 |
| WO | 2009079796 | A1 | 7/2009 |
| WO | 2010/060719 | A1 | 6/2010 |
| WO | 2010086189 | A2 | 8/2010 |
| WO | 2010149743 | A2 | 12/2010 |
| WO | 2010149745 | A1 | 12/2010 |
| WO | 2011008974 | A2 | 1/2011 |
| WO | 2011/020079 | A1 | 2/2011 |
| WO | 2011/045378 | A1 | 4/2011 |
| WO | 2011/045381 | A1 | 4/2011 |
| WO | 2011050168 | A2 | 4/2011 |
| WO | 2011/098592 | A1 | 8/2011 |
| WO | 2012006596 | A2 | 1/2012 |
| WO | 2012158613 | A1 | 11/2012 |
| WO | 2013/139911 | A1 | 9/2013 |
| WO | 2013/139916 | A1 | 9/2013 |
| WO | 2013135615 | A1 | 9/2013 |
| WO | 2014005643 | A1 | 1/2014 |
| WO | 2014160463 | A1 | 10/2014 |
| WO | 2014174018 | A1 | 10/2014 |
| WO | 2014202570 | A1 | 12/2014 |
| WO | 2015013551 | A1 | 1/2015 |
| WO | 2015040002 | A1 | 3/2015 |
| WO | 2017174564 | A1 | 10/2017 |

OTHER PUBLICATIONS

Letarov et al., "The Carboxy-Terminal Domain Initiates Trimerization of Bacteriophage T4 Fibritin," Biochemistry (Moscow), vol. 64, No. 7, pp. 817-823 (1999).
Guthe et al., "Very Fast Folding and Association of a Trimerization Domain from Bacteriophage T4 Fibritin," J. Mol. Biol., vol. 337, pp. 905-915 (2004).
"Database UniProt Accession W8CJC7," http://ibis.internal.epo.org/exam/dbfetch.jsp?id=UNIPROT:W8CJC7, Download date: Aug. 12, 2015, 1 page.
Widjaja et al., "Recombinant soluble Respiratory Syncytial Virus F Protein That Lacks Heptad Repeat B, Contains a GCN4 Trimerization Motif and Is Not Cleaved Displays Prefusion-Like Characteristics," PLOS ONE, 20 pages, Jun. 24, 2015.
Written Opinion dated Oct. 10, 2016 in Int'l Application No. PCT/EP2016/066104.
Int'l Search Report dated Oct. 10, 2016 in Int'l Application No. PCT/EP2016/066104.
Written Opinion dated Oct. 12, 2016 in Int'l Application No. PCT/EP2016/066098.
Int'l Search Report dated Oct. 12, 2016 in Int'l Application No. PCT/EP2016/066098.
Suzuki et al., "An Isoleucine Zipper Peptide Forms a Native-like Triple Stranded Coiled Coil in Solution," Protein Engineering, vol. 11, No. 11, pp. 1051-1055 (1998).

Dames et al., "NMR Structure of a Parallel Homotrimeric Coiled Coil," Nature Structural Biology, vol. 5, No. 8, pp. 687-691 (Aug. 1998).
Calder et al., "Electron Microscopy Of The Human Respiratory Syncytial Virus Fusion Protein and Complexes That It Forms With Monoclonal Antibodies," Virology, vol. 271, pp. 122-131 (2000).
Harbury et al., "A Switch Between Two-, Three-, and Four-Stranded Coiled Coils in GCN4 Leucine Zipper Mutants," Science, vol. 262, pp. 1401-1407.
O'Shea et al., "Evidence That the Leucine Zipper Is a Coiled Coil," Science, vol. 243, pp. 538-542 (Jan. 27, 1989).
Database EMBL, Aug. 28, 1995, Human respiratory syncytial virus, strain RSB89-1734, fusion protein (F) mRNA, complete CDS, XP002729919.
Int'l Search Report and Written Opinion dated Oct. 9, 2014 in Int'l Application No. PCT/EP2014/062655.
Int'l Search Report and Written Opinion dated Aug. 12, 2014 in Int'l Application No. PCT/EP2014/058353.
Magro et al., "Neutralizing Antibodies Against the Preactive Form of Respiratory Syncytial Virus Protein Offer Unique Possibilities for Clinical Intervention," PNAS, vol. 109, No. 8, pp. 3089-3094 (Feb. 21, 2012).
Yin et al., "Structure of the Parainfluenza Virus 5 F Protein in its Metastable, Prefusion Conformation," Nature, vol. 439, pp. 38-44 (Jan. 5, 2006).
Ngwuta et al, "Prefusion F-Specific Antibodies Determine the Magnitude of RSV Neutralizing Activity in Human Sera," Science Translational Medicine, vol. 7, No. 309, pp. 1-9 (2015).
Int'l Search Report and Written Opinion dated Jun. 12, 2017 in Int'l Application No. PCT/EP2017/057962.
Abbink et al, "Comparative Seroprevalence and Immunogenicity of Six Rare Serotype Recombinant Adenovirus Vaccine Vectors from Subgroups B and D," Journal of Virology, vol. 81, No. 9, pp. 4654-4663 (May 2007).
Abrahamsen et al, "Construction of an Adenovirus Type 7a E1A-Vector," Journal of Virology, vol. 71, No. 11, pp. 3946-8951 (Nov. 1997).
Altaras et al, "Production and Formulation of Adenovirus Vectors," Advances in Biochemical Engineering / Biotechnology, vol. 99, pp. 193-260 (2005).
Brough et al, "A Gene Transfer Vector-Cell Line System for Complete Functional Complementation of Adenovirus Early Regions E1 and E4," Journal of Virology, vol. 70, No. 9, pp. 6497-6501 (Sep. 1996).
Fallaux et al, "New Helper Cells and Matched Early Region 1-Deleted Adenovirus Vectors Prevent Generation of Replication-Competent Adenoviruses," Human Gene Therapy, vol. 9, pp. 1909-1917 (Sep. 1998).
Gao et al, "A Cell Line for High-Yield Production of E1-Deleted Adenovirus Vectors without the Emergence of Replication-Competent Virus," Human Gene Therapy, vol. 11, pp. 213-219 (Jan. 2000).
Goerke et al, "Development of a Novel Adenovirus Purification Process Utilizing Selective Precipitation of Cellular DNA," Biotechnology and Bioengineering, vol. 91, pp. 12-21 (2005).
Havenga et al, "Novel replication-incompetent adenoviral B-group vectors: high vector stability and yield in PER.C6 cells," Journal of General Virology, vol. 87, pp. 2135-2143 (2006).
Hoganson et al, "Development of a Stable Adenoviral Vector Formulation," BioProcessing Journal, vol. 1, No. 1, pp. 43-48 (Mar. 2002).
Kim et al, "Single mucosal immunization of recombinant adenovirus-based vaccine expressing F1 protein fragment induces protective mucosal immunity against respiratory syncytial virus infection," Vaccine, vol. 28, pp. 3801-3808 (2010).
Kohlmann et al, "Protective Efficacy and Immunology of an Adenoviral Vector Vaccine Encoding the Codon-Optimized F Protein of Respiratory Syncytial Virus," Journal of Virology, vol. 83, No. 23, pp. 12601-12610 (Dec. 2009).
Konz et al, "Serotype Specificity of Adenovirus Purification Using Anion-Exchange Chromatography," Human Gene Therapy, vol. 16, pp. 1346-1353 (Nov. 2005).

(56) References Cited

OTHER PUBLICATIONS

Konz et al, "Scaleable Purification of Adenovirus Vectors," Methods in Molecular Biology, vol. 434, No. 2, pp. 13-23 (2008).
Krarup et al, "A Highly Stable Prefusion RSV F Vaccine Derived from Structural Analysis of the Fusion Mechanism," Nature Communications, vol. 6, pp. 1-11 (Sep. 2015).
Nan et al, "Development of an Ad7 cosmid system and generation of an Ad7LE1LE3HIVMN env/rev recombinant virus," Gene Therapy, vol. 10, pp. 326-336 (2003).
Pemberton et al, "Cytoxic T Cell Specificity for Respiratory Syncytial Virus Proteins: Fusion Protein is an Important Target Antigen," Journal of General Virology, vol. 68, pp. 2177-2182 (1987).
Solabomi et al, "The Oligomerization Domain of C4-Binding Protein (C4bp) Acts as an Adjuvant, and the Fusion Protein Comprised of the 19-Kilodalton Merozoite Surface Protein 1 Fused with the Murine C4bp Domain Protects Mice against Malaria," Infection and Immunity, vol. 76, No. 8, pp. 3817-3823 (Aug. 2008).
Vogels et al, "Replication-Deficient Human Adenovirus Type 35 Vectors for Gene Transfer and Vaccination: Efficient Human Cell Infection and Bypass of Preexisting Adenovirus Immunity," Journal of Virology, vol. 77, No. 15, pp. 8263-8271 (Aug. 2003).
Yu et al, "Single Intranasal Immunization with Recombinant Adenovirus-Based Vaccine Induces Protective Immunity against Respiratory Syncytial Virus Infection," Journal of Virology, vol. 82, No. 5, pp. 2350-2357 (Mar. 2008).
Int'l Search Report and Written Opinion dated Jun. 12, 2017 in Int'l Application No. PCT/EP2017/057957.
Krause et al, "A Broadly Neutralizing Human Monclonal Antibody That Recognizes a Conserved, Novel Epitope on the Globular Head of the Influenza H1N1 Virus Hemagglutinin," Journal of Virology, vol. 85, No. 20, pp. 10905-10908 (Oct. 2011).
McLellan et al, "Structure of Respiratory Syncytial Virus Fusion Glycoprotein in the Postfusion Conformation Reveals Preservation of Neutralizing Epitopes," Journal of Virology, vol. 85, No. 15, pp. 7788-7796 (Aug. 2011).
Database Geneseq (online) "RSV fusion protein N67I S215P, RSV CL57-v224, fibritin, SEQ: 74", XP002761983, retrieved from EBI accession No. GSP:BBP75438, Database accession No. BBP75438 sequence.
Bangari et al., "Development of nonhuman adenoviruses as vaccine vectors", Vaccine, 24(7), pp. 849-862, 2006.
Cohen et al., "Chimpanzee adenovirus CV-68 adapted as a gene delivery vector interacts with the coxsackievirus and adenovirus receptor", Journal of General Virology, 83, pp. 151-155, 2002.
Farina et al., "Replication-Defective Vector Based on a Chimpanzee Adenovirus", Journal of Virology, vol. 75, No. 23, pp. 11603-11613, Dec. 2001.
Kobinger et al., "Chimpanzee adenovirus vaccine protects against Zaire Ebola Virus", Science Direct, Virology, 346, pp. 394-401, 2006.
Lasaro et al., "New Insights on Adenovirus as Vaccine Vectors", Molecular Therapy, vol. 17, No. 8, pp. 1333-1339, Aug. 2009.
Tatsis et al., "A CD46-binding Chimpanzee Adenovirus Vector as a Vaccine Carrier", American Society of Gene Therapy, vol. 15, No. 3, pp. 608-617, Mar. 2007.
Widjojatomodjo et al., "Recombianant Low-seroprevalent adenoviral vectors Ad26 and Ad35 expressing the espiratory syncytial virus (RSV) fusion protein induce protective immunity against RSV infection in cotton rats", Vaccine, 33, pp. 5406-5414, 2015.
Green et al., "Safety and Immunogenicity of novel respiratory syncytial virus (RSV) vaccines based on the RSV viral proteins F, N and M2-1 encoded by simian adenovirus (PanAd3-RSV) and MVA (MVA-RSV): protocol for an open-label, dose-escalation, single-centre, phase 1 clinical trial in healthy adults", BMJ Open, 13 pages, Oct. 2015.
Grunwald et al., "Novel Vaccine Regimen Elicits Strong Airway Immune Responses and Control of Respiratory Syncytial Virus in Nonhuman Primates", Journal of Virology, vol. 88, No. 8, pp. 3997-4007, Apr. 2014.
Int'l Search Report and Written Opinion dated Sep. 8, 2018 in Int'l, Application No. PCT/EP2018/062604.
Neuzil, "Progress toward a Respiratory Syncytial Virus Vaccine", Clinical and Vaccine Immunology, vol. 23, pp. 186-188, 2016.
Gilman et al., "Rapid profiling of RSV antibody repertoires from the memory B cells of naturally infected adult donors", Science Immunology, 11 pages, Dec. 2016.
Openshaw et al., "Protective and Harmful Immunity to RSV Infection", Annu Rev. Immunol, vol. 35, pp. 501-532, 2017.
Janssen Vaccines & Prevention B.V.: A Study to Evaluate the Safety, Tolerability and Immunogenicity of Two Vaccinations of Ad26.RSV. preF One Year Apart in Adults Aged 60 Years and Older in Stable Health, Oct. 2016, retrieved from the Internet: http://clinicaltrials.gov/ct2/show/record/NCT02926430 (retrived on Nov. 30, 2018.
Int'l Search Report and Written Opinion dated Dec. 17, 2018 in Int'l Application No. PCT/EP2018/074710.
Comparison to Sequence 16, Application US/12517194; Pat. No. 8772256 (Year: 2014) 4 pages.
International Search Report and Written Opinion issued in PCT/EP2017/062875, dated Aug. 14, 2017, 10 pages.

SEQUENCE LISTING

<160> NUMBER OF SEQ ID NOS: 21

<210> SEQ ID NO 1
<211> LENGTH: 12
<212> TYPE: PRT
<213> ORGANISM: Artificial Sequence
<220> FEATURE:
<223> OTHER INFORMATION: CR9501 HCDR1

<400> SEQUENCE: 1

Gly Ala Ser Ile Asn Ser Asp Asn Tyr Tyr Trp Thr
1               5                   10

<210> SEQ ID NO 2
<211> LENGTH: 16
<212> TYPE: PRT
<213> ORGANISM: Artificial Sequence
<220> FEATURE:
<223> OTHER INFORMATION: CR9501 HCDR2

<400> SEQUENCE: 2

His Ile Ser Tyr Thr Gly Asn Thr Tyr Tyr Thr Pro Ser Leu Lys Ser
1               5                   10                  15

<210> SEQ ID NO 3
<211> LENGTH: 15
<212> TYPE: PRT

```
<213> ORGANISM: Artificial Sequence
<220> FEATURE:
<223> OTHER INFORMATION: CR9501 HCDR3

<400> SEQUENCE: 3

Cys Gly Ala Tyr Val Leu Ile Ser Asn Cys Gly Trp Phe Asp Ser
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: CR9501 LCDR1

<400> SEQUENCE: 4

Gln Ala Ser Gln Asp Ile Ser Thr Tyr Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CR9501 LCDR2

<400> SEQUENCE: 5

Gly Ala Ser Asn Leu Glu Thr
1               5

<210> SEQ ID NO 6
<211> LENGTH: 9
<212> TYPE: PRT
<213> ORGANISM: Artificial Sequence
<220> FEATURE:
<223> OTHER INFORMATION: CR9501 LCDR3

<400> SEQUENCE: 6

Gln Gln Tyr Gln Tyr Leu Pro Tyr Thr
1               5

<210> SEQ ID NO 7
<211> LENGTH: 10
<212> TYPE: PRT
<213> ORGANISM: Artificial Sequence
<220> FEATURE:
<223> OTHER INFORMATION: CR9502 HCDR1

<400> SEQUENCE: 7

Gly Phe Thr Phe Ser Gly His Thr Ile Ala
1               5                   10

<210> SEQ ID NO 8
<211> LENGTH: 17
<212> TYPE: PRT
<213> ORGANISM: Artificial Sequence
<220> FEATURE:
<223> OTHER INFORMATION: CR9502 HCDR2

<400> SEQUENCE: 8

Trp Val Ser Thr Asn Asn Gly Asn Thr Glu Tyr Ala Gln Lys Ile Gln
1               5                   10                  15
Gly

<210> SEQ ID NO 9
<211> LENGTH: 12
```

```
<212> TYPE: PRT
<213> ORGANISM: Artificial Sequence
<220> FEATURE:
<223> OTHER INFORMATION: CR9502 HCDR3

<400> SEQUENCE: 9

Glu Trp Leu Val Met Gly Gly Phe Ala Phe Asp His
1               5                   10

<210> SEQ ID NO 10
<211> LENGTH: 11
<212> TYPE: PRT
<213> ORGANISM: Artificial Sequence
<220> FEATURE:
<223> OTHER INFORMATION: CR9502 LCDR1

<400> SEQUENCE: 10

Gly Ala Asn Asn Ile Gly Ser Gln Asn Val His
1               5                   10

<210> SEQ ID NO 11
<211> LENGTH: 7
<212> TYPE: PRT
<213> ORGANISM: Artificial Sequence
<220> FEATURE:
<223> OTHER INFORMATION: CR9502 LCDR2

<400> SEQUENCE: 11

Asp Asp Arg Asp Arg Pro Ser
1               5

<210> SEQ ID NO 12
<211> LENGTH: 12
<212> TYPE: PRT
<213> ORGANISM: Artificial Sequence
<220> FEATURE:
<223> OTHER INFORMATION: CR9502 LCDR3

<400> SEQUENCE: 12

Gln Val Trp Asp Ser Ser Arg Asp Gln Ala Val Ile
1               5                   10

<210> SEQ ID NO 13
<211> LENGTH: 574
<212> TYPE: PRT
<213> ORGANISM: Artificial Sequence
<220> FEATURE:
<223> OTHER INFORMATION: RSV F protein full length sequence

<400> SEQUENCE: 13

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110
```

```
Arg Phe Met Asn Tyr Thr Leu Asn Asn Ala Lys Lys Thr Asn Val Thr
            115                 120                 125
Leu Ser Lys Lys Arg Lys Arg Arg Phe Leu Gly Phe Leu Leu Gly Val
        130                 135                 140
Gly Ser Ala Ile Ala Ser Gly Val Ala Val Ser Lys Val Leu His Leu
145                 150                 155                 160
Glu Gly Glu Val Asn Lys Ile Lys Ser Ala Leu Leu Ser Thr Asn Lys
                165                 170                 175
Ala Val Val Ser Leu Ser Asn Gly Val Ser Val Leu Thr Ser Lys Val
            180                 185                 190
Leu Asp Leu Lys Asn Tyr Ile Asp Lys Gln Leu Leu Pro Ile Val Asn
        195                 200                 205
Lys Gln Ser Cys Ser Ile Ser Asn Ile Glu Thr Val Ile Glu Phe Gln
210                 215                 220
Gln Lys Asn Asn Arg Leu Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
        275                 280                 285
Met Ser Ile Ile Lys Glu Glu Val Leu Ala Tyr Val Val Gln Leu Pro
290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
        355                 360                 365
Thr Met Asn Ser Leu Thr Leu Pro Ser Glu Val Asn Leu Cys Asn Val
370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
        435                 440                 445
Thr Val Ser Val Gly Asn Thr Leu Tyr Tyr Val Asn Lys Gln Glu Gly
450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Lys Ser Asp Glu Leu
            500                 505                 510
Leu His Asn Val Asn Ala Val Lys Ser Thr Thr Asn Ile Met Ile Thr
        515                 520                 525
```

-continued

Thr Ile Ile Ile Val Ile Ile Val Ile Leu Leu Ser Leu Ile Ala Val
        530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 14
<211> LENGTH: 27
<212> TYPE: PRT
<213> ORGANISM: Artificial Sequence
<220> FEATURE:
<223> OTHER INFORMATION: fibritin

<400> SEQUENCE: 14

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 15
<211> LENGTH: 574
<212> TYPE: PRT
<213> ORGANISM: Artificial Sequence
<220> FEATURE:
<223> OTHER INFORMATION: RSV F protein B1 full length sequence

<400> SEQUENCE: 15

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Asn Arg Glu Phe Ser Val Asn
225                 230                 235                 240

```
Ala Gly Val Thr Thr Pro Leu Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
                500                 505                 510

Leu His Asn Val Asn Thr Gly Lys Ser Thr Thr Asn Ile Met Ile Thr
            515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570

<210> SEQ ID NO 16
<211> LENGTH: 228
<212> TYPE: PRT
<213> ORGANISM: Artificial Sequence
<220> FEATURE:
<223> OTHER INFORMATION: CR9501 heavy chain

<400> SEQUENCE: 16

Gln Val Gln Leu Val Gln Ser Gly Pro Gly Leu Val Lys Pro Ser Gln
1               5                   10                  15

Thr Leu Ala Leu Thr Cys Asn Val Ser Gly Ala Ser Ile Asn Ser Asp
            20                  25                  30
```

Asn Tyr Tyr Trp Thr Trp Ile Arg Gln Arg Pro Gly Gly Gly Leu Glu
            35                  40                  45

Trp Ile Gly His Ile Ser Tyr Thr Gly Asn Thr Tyr Tyr Thr Pro Ser
 50                  55                  60

Leu Lys Ser Arg Leu Ser Met Ser Leu Glu Thr Ser Gln Ser Gln Phe
 65                  70                  75                  80

Ser Leu Arg Leu Thr Ser Val Thr Ala Ala Asp Ser Ala Val Tyr Phe
                 85                  90                  95

Cys Ala Ala Cys Gly Ala Tyr Val Leu Ile Ser Asn Cys Gly Trp Phe
                100                 105                 110

Asp Ser Trp Gly Gln Gly Thr Gln Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
                195                 200                 205

Asn Val Asn His Lys Pro Ser Asn Thr Lys Val Asp Lys Lys Val Glu
    210                 215                 220

Pro Lys Ser Cys
225

<210> SEQ ID NO 17
<211> LENGTH: 214
<212> TYPE: PRT
<213> ORGANISM: Artificial Sequence
<220> FEATURE:
<223> OTHER INFORMATION: CR9501 light chain

<400> SEQUENCE: 17

Glu Ile Val Met Thr Gln Ser Pro Ser Ser Leu Ser Ala Ser Ile Gly
 1               5                  10                  15

Asp Arg Val Thr Ile Thr Cys Gln Ala Ser Gln Asp Ile Ser Thr Tyr
                 20                  25                  30

Leu Asn Trp Tyr Gln Gln Lys Pro Gly Gln Ala Pro Arg Leu Leu Ile
            35                  40                  45

Tyr Gly Ala Ser Asn Leu Glu Thr Gly Val Pro Ser Arg Phe Thr Gly
 50                  55                  60

Ser Gly Tyr Gly Thr Asp Phe Ser Val Thr Ile Ser Ser Leu Gln Pro
 65                  70                  75                  80

Glu Asp Ile Ala Thr Tyr Tyr Cys Gln Gln Tyr Gln Tyr Leu Pro Tyr
                 85                  90                  95

Thr Phe Ala Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 18
<211> LENGTH: 224
<212> TYPE: PRT
<213> ORGANISM: Artificial Sequence
<220> FEATURE:
<223> OTHER INFORMATION: CR9502 heavy chain

<400> SEQUENCE: 18

Glu Val Gln Leu Leu Gln Ser Gly Ala Glu Leu Lys Lys Pro Gly Ala
1               5                   10                  15

Ser Val Lys Ile Ser Cys Lys Thr Ser Gly Phe Thr Phe Ser Gly His
            20                  25                  30

Thr Ile Ala Trp Val Arg Gln Ala Pro Gly Gln Gly Leu Glu Trp Met
        35                  40                  45

Gly Trp Val Ser Thr Asn Asn Gly Asn Thr Glu Tyr Ala Gln Lys Ile
    50                  55                  60

Gln Gly Arg Val Thr Met Thr Met Asp Thr Ser Thr Ser Thr Val Tyr
65                  70                  75                  80

Met Glu Leu Arg Ser Leu Thr Ser Asp Asp Thr Ala Val Tyr Phe Cys
                85                  90                  95

Ala Arg Glu Trp Leu Val Met Gly Gly Phe Ala Phe Asp His Trp Gly
            100                 105                 110

Gln Gly Thr Leu Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

<210> SEQ ID NO 19
<211> LENGTH: 215
<212> TYPE: PRT
<213> ORGANISM: Artificial Sequence
<220> FEATURE:
<223> OTHER INFORMATION: CR9502 light chain

<400> SEQUENCE: 19

Gln Ser Val Leu Thr Gln Ala Ser Ser Val Ser Val Ala Pro Gly Gln
1               5                   10                  15

Thr Ala Arg Ile Thr Cys Gly Ala Asn Asn Ile Gly Ser Gln Asn Val

```
                 20                  25                  30
His Trp Tyr Gln Gln Lys Pro Gly Gln Ala Pro Val Leu Val Tyr
         35                  40                  45

Asp Arg Asp Arg Pro Ser Gly Ile Pro Asp Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Arg Asp Gln
                 85                  90                  95

Ala Val Ile Phe Gly Gly Gly Thr Lys Leu Thr Val Leu Gly Gln Pro
             100                 105                 110

Lys Ala Ala Pro Ser Val Thr Leu Phe Pro Pro Ser Ser Glu Glu Leu
         115                 120                 125

Gln Ala Asn Lys Ala Thr Leu Val Cys Leu Ile Ser Asp Phe Tyr Pro
     130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                 165                 170                 175

Ala Ser Ser Tyr Leu Ser Leu Thr Pro Glu Gln Trp Lys Ser His Arg
             180                 185                 190

Ser Tyr Ser Cys Gln Val Thr His Glu Gly Ser Thr Val Glu Lys Thr
         195                 200                 205

Ile Ala Pro Thr Glu Cys Ser
     210                 215

<210> SEQ ID NO 20
<211> LENGTH: 574
<212> TYPE: PRT
<213> ORGANISM: Artificial Sequence
<220> FEATURE:
<223> OTHER INFORMATION: RSV F protein CL57-v224 full length sequence

<400> SEQUENCE: 20

Met Glu Leu Pro Ile Leu Lys Thr Asn Ala Ile Thr Thr Ile Leu Ala
 1               5                  10                  15

Ala Val Thr Leu Cys Phe Ala Ser Ser Gln Asn Ile Thr Glu Glu Phe
                 20                  25                  30

Tyr Gln Ser Thr Cys Ser Ala Val Ser Lys Gly Tyr Leu Ser Ala Leu
             35                  40                  45

Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Ala Asn Asn Arg Ala Arg Arg Glu Leu Pro
             100                 105                 110

Arg Phe Met Asn Tyr Thr Leu Asn Asn Thr Lys Asn Asn Val Thr
         115                 120                 125

Leu Ser Lys Lys Arg Lys Arg Arg Phe Leu Gly Phe Leu Leu Gly Val
     130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
```

165                 170                 175
Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
        210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
        290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Ile
        370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Val Gly Lys Ser Thr Thr Asn Ile Met Ile Thr
        515                 520                 525

Thr Ile Ile Ile Val Ile Ile Val Ile Leu Leu Leu Ile Ala Val
        530                 535                 540

Gly Leu Phe Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 21

<211> LENGTH: 544
<212> TYPE: PRT
<213> ORGANISM: Artificial Sequence
<220> FEATURE:
<223> OTHER INFORMATION: RSV F, N67I, S215P, D486N, and 357K and 371Y

<400> SEQUENCE: 21

```
Met Glu Leu Leu Ile Leu Lys Ala Asn Ala Ile Thr Thr

```
Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asn Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540
```

STABILIZED PRE-FUSION RSV F PROTEINS

CROSS-REFERENCE TO RELATED APPLICATION

This application is a Section 371 of International Application No. PCT/EP2017/062875, filed May 29, 2017, which was published in the English language on Dec. 7, 2017 under International Publication No. WO 2017/207480 A1, and claims priority under 35 U.S.C. § 119(b) to European Application No. 16172008.1, filed May 30, 2016, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing 688097_559US", creation date of Nov. 29, 2018, and having a size of 30.9 KB. The sequence listing submitted via EFS-Web is part of the specification and is herein incorporated by reference in its entirety.

The present invention relates to the field of medicine. The invention in particular relates to recombinant pre-fusion RSV F proteins, to nucleic acid molecules encoding the RSV F proteins, and uses thereof, e.g. in vaccines.

BACKGROUND OF THE INVENTION

After discovery of the respiratory syncytial virus (RSV) in the 1950s, the virus soon became a recognized pathogen associated with lower and upper respiratory tract infections in humans. Worldwide, it is estimated that 64 million RSV infections occur each year resulting in 160,000 deaths (WHO Acute Respiratory Infections Update September 2009). The most severe disease occurs particularly in premature infants, the elderly and immunocompromised individuals. In children younger than 2 years, RSV is the most common respiratory tract pathogen, accounting for approximately 50% of the hospitalizations due to respiratory infections, and the peak of hospitalization occurs at 2-4 months of age. It has been reported that almost all children have been infected by RSV by the age of two. Repeated infection during lifetime is attributed to ineffective natural immunity. In the elderly, the RSV disease burden is similar to those caused by non-pandemic influenza A infections.

RSV is a paramyxovirus, belonging to the subfamily of pneumovirinae. Its genome encodes for various proteins, including the membrane proteins known as RSV Glycoprotein (G) and RSV fusion (F) protein which are the major antigenic targets for neutralizing antibodies. Antibodies against the fusion-mediating part of the F1 protein can prevent virus uptake in the cell and thus have a neutralizing effect.

RSV F fuses the viral and host-cell membranes by irreversible protein refolding from the labile pre-fusion conformation to the stable post-fusion conformation. Structures of both conformations have been determined for RSV F (McLellan J S, et al. *Science* 342, 592-598 (2013); McLellan J S, et al. *Nat Struct Mol Biol* 17, 248-250 (2010); McLellan J S, et al. *Science* 340, 1113-1117 (2013); Swanson K A, et al. *Proceedings of the National Academy of Sciences of the United States of America* 108, 9619-9624 (2011)), as well as for the fusion proteins from related paramyxoviruses, providing insight into the mechanism of this complex fusion machine. Like other type I fusion proteins, the inactive precursor, RSV $F_0$, requires cleavage during intracellular maturation by a furin-like protease. RSV F contains two furin sites, which leads to three proteins: F2, p27 and F1, with the latter containing a hydrophobic fusion peptide (FP) at its N-terminus. In order to refold from the pre-fusion to the post-fusion conformation, the refolding region 1 (RR1) between residue 137 and 216, that includes the FP and heptad repeat A (HRA) has to transform from an assembly of helices, loops and strands to a long continuous helix. The FP, located at the N-terminal segment of RR1, is then able to extend away from the viral membrane and insert into the proximal membrane of the target cell. Next, the refolding region 2 (RR2), which forms the C-terminal stem in the pre-fusion F spike and includes the heptad repeat B (HRB), relocates to the other side of the RSV F head and binds the HRA coiled-coil trimer with the HRB domain to form the six-helix bundle. The formation of the RR1 coiled-coil and relocation of RR2 to complete the six-helix bundle are the most dramatic structural changes that occur during the refolding process.

A vaccine against RSV infection is currently not available, but is desired due to the high disease burden. The RSV fusion glycoprotein (RSV F) is an attractive vaccine antigen it is the principal target of neutralizing antibodies in human sera. Most neutralizing antibodies in human sera are directed against the pre-fusion conformation, but due to its instability the pre-fusion conformation has a propensity to prematurely refold into the post-fusion conformation, both in solution and on the surface of the virions. As indicated above, crystal structures have revealed a large conformational change between the pre-fusion and post-fusion states. The magnitude of the rearrangement suggested that only a portion of antibodies directed to the post-fusion conformation of RSV-F will be able to cross react with the native conformation of the pre-fusion spike on the surface of the virus. Accordingly, efforts to produce a vaccine against RSV have focused on developing vaccines that contain pre-fusion forms of RSV F protein (see, e.g., WO20101149745, WO2010/1149743, WO2009/1079796, WO2012/158613). However, these efforts have not yet yielded stable pre-fusion RSV F proteins that could be used as candidates for testing in humans.

Therefore, a need remains for efficient vaccines against RSV, in particular vaccines comprising RSV F proteins in the pre-fusion conformation. The present invention aims at providing such stable pre-fusion RSV F proteins for use in vaccinating against RSV in a safe and efficacious manner.

SUMMARY OF THE INVENTION

The present invention provides stable, recombinant, pre-fusion respiratory syncytial virus (RSV) fusion (F) proteins, i.e. recombinant RSV F proteins that are stabilized in the pre-fusion conformation, and fragments thereof. The RSV F proteins, or fragments thereof, comprise at least one epitope that is specific to the pre-fusion conformation F protein. In certain embodiments, the pre-fusion RSV F proteins are soluble proteins. In certain embodiments, the RSV F proteins are trimers. In certain embodiments the RSV F proteins are multimers of trimeric RSV F proteins. The invention also provides nucleic acid molecules encoding the pre-fusion RSV F proteins, or fragments thereof, as well as vectors comprising such nucleic acid molecules.

The invention also relates to compositions, preferably immunogenic compositions, comprising a RSV F protein, a nucleic acid molecule and/or a vector, and to the use thereof in inducing an immune response against RSV F protein, in particular to the use thereof as a vaccine. The invention also relates to methods for inducing an anti-respiratory syncytial virus (RSV) immune response in a subject, comprising administering to the subject an effective amount of a pre-fusion RSV F protein, a nucleic acid molecule encoding said RSV F protein, and/or a vector comprising said nucleic acid molecule. Preferably, the induced immune response is characterized by neutralizing antibodies to RSV and/or protective immunity against RSV. In particular aspects, the invention relates to a method for inducing anti-respiratory syncytial virus (RSV) F antibodies in a subject, comprising administering to the subject an effective amount of an immunogenic composition comprising a pre-fusion RSV F protein, a nucleic acid molecule encoding said RSV F protein, and/or a vector comprising said nucleic acid molecule.

DETAILED DESCRIPTION OF THE INVENTION

Figure 1:
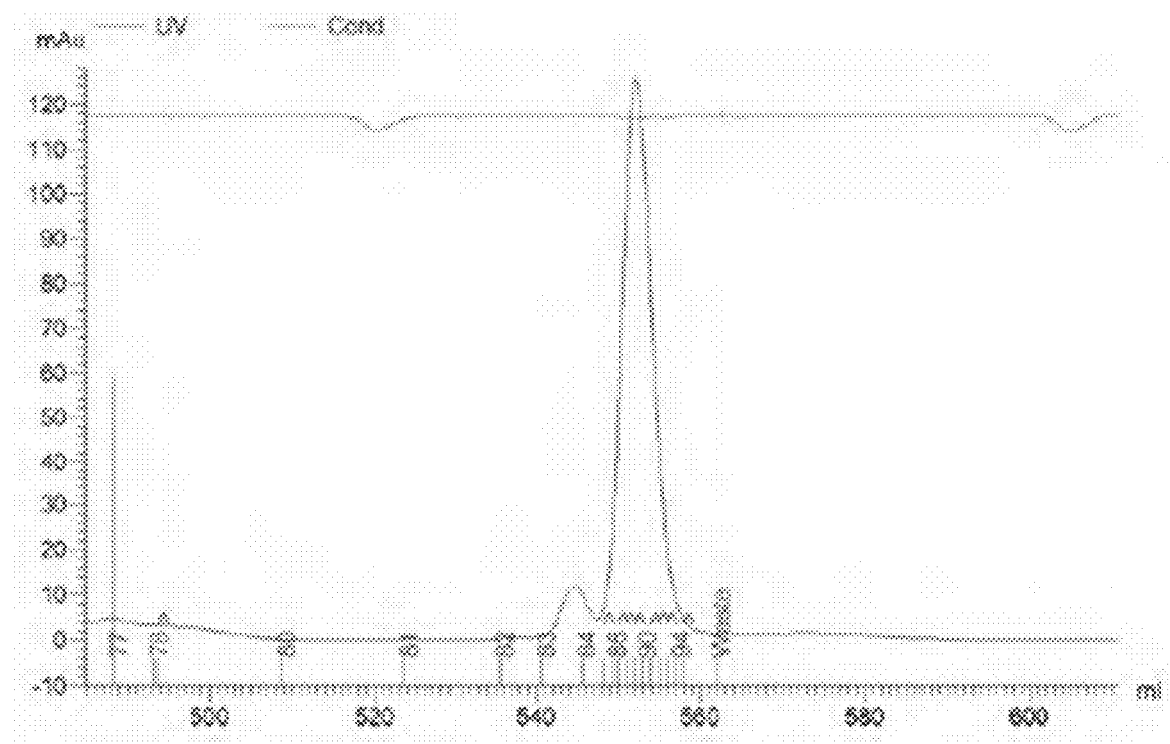
FIG. 1: Purification of protein F with mutations N67I, S215P, T357K, N371Y, and D486N. Superdex200 gel filtration chromatogram of the eluate from the ion-exchange column. The arrow indicates the collected peak.

The fusion protein (F) of the respiratory syncytial virus (RSV) is involved in fusion of the viral membrane with a host cell membrane, which is required for infection. RSV F mRNA is translated into a 574 amino acid precursor protein designated F0, which contains a signal peptide sequence at the N-terminus (e.g. amino acid residues 1-26 of SEQ ID NO: 13) which is removed by a signal peptidase in the endoplasmic reticulum. F0 is cleaved at two sites (between amino acid residues 109/110 and 136/137) by cellular proteases (in particular furin, or furin-like)) removing a short glycosylated intervening sequence (also referred to a p27 region, comprising the amino acid residues 110 to 136, and generating two domains or subunits designated F1 and F2. The F1 domain (amino acid residues 137-574) contains a hydrophobic fusion peptide at its N-terminus and the C-terminus contains the transmembrane (TM) (amino acid residues 530-550) and cytoplasmic region (amino acid residues 551-574). The F2 domain (amino acid residues 27-109) is covalently linked to F1 by two disulfide bridges. The F1-F2 heterodimers are assembled as homotrimers in the virion.

A vaccine against RSV infection is currently not yet available. One potential approach to producing a vaccine is a subunit vaccine based on purified RSV F protein. However, for this approach it is desirable that the purified RSV F protein is in a conformation which resembles the conformation of the pre-fusion state of RSV F protein, which is stable over time and can be produced in sufficient quantities. In addition, for a soluble, subunit-based vaccine, the RSV F protein needs to be truncated by deletion of the transmembrane (TM) and the cytoplasmic region to create a soluble secreted F protein (sF). Because the TM region is responsible for membrane anchoring and stability, the anchorless soluble F protein is considerably more labile than the full-length protein and will readily refold into the post-fusion end-state. In order to obtain soluble F protein in the stable pre-fusion conformation that shows high expression levels and high stability, the pre-fusion conformation thus needs to be stabilized. Because also the full length (membrane-bound) RSV F protein is metastable, the stabilization of the pre-fusion conformation is also desirable for the full length RSV F protein, e.g. for any life attenuated or vector based vaccine approach.

For the stabilization of soluble RSV F, that is cleaved into the F1 and F2 subunit, in the pre-fusion conformation, a fibritin-based trimerization domain was fused to the C-terminus of the soluble RSV-F C-terminal end (McLellan et al., Nature Struct. Biol. 17: 2-248-250 (2010); McLellan et al., Science 340(6136):1113-7 (2013)). This fibritin domain or 'Foldon' is derived from T4 fibritin and was described earlier as an artificial natural trimerization domain (Letarov et al., Biochemistry Moscow 64: 817-823 (1993); S-Guthe et al., J. Mol. Biol. 337: 905-915. (2004)). However, the trimerization domain does not result in stable pre-fusion RSV-F protein (Krarup et al., Nature Comm. 6:8143, (2015)). Moreover, these efforts have not yet resulted in candidates suitable for testing in humans.

Recently, we described combinations of several mutations that are capable of stabilizing the RSV F protein in the pre-fusion conformation (WO2014/174018 and WO2014/202570). Thus, stable pre-fusion RSV F proteins have been described comprising a mutation of the amino acid residue on position 67 and/or a mutation of the amino acid residue on position 215, preferably a mutation of amino acid residue N/T on position 67 into I and/or a mutation of amino acid residue S on position 215 into P. In addition, soluble pre-fusion RSV F proteins have been described comprising a truncated F1 domain, and comprising a mutation of the amino acid residue on position 67 and/or a mutation of the amino acid residue on position 215, preferably a mutation of amino acid residue N/T on position 67 into I and/or a mutation of amino acid residue S on position 215 into P, wherein the protein comprises a heterologous trimerization domain linked to said truncated F1 domain. Additional pre-fusion RSV F proteins have been described, wherein the proteins comprise at least one further mutation, such as a mutation of the amino acid residue D on position 486 into N.

According to the present invention it has been found that the introduction of two other mutations, i.e. on positions 357 and 371 (numbering according to SEQ ID NO: 13) also stabilizes the protein in the pre-fusion conformation.

The present invention thus provides recombinant pre-fusion F proteins comprising a mutation of the amino acid residue on position 215, in particular a mutation of the amino acid S on position 215 into P (S215P), in combination with a mutation of the amino acids on positions 357, in particular a mutation of the amino acid T on position 357 into K (T357K) and a mutation of the amino acid on position 371, in particular a mutation of the amino acid N on position 371 into Y (N371Y).

The present invention thus provides a unique combination of mutations to provide recombinant stable pre-fusion RSV F proteins, i.e. RSV F proteins that are stabilized in the pre-fusion conformation, or fragments thereof. The stable pre-fusion RSV F proteins of the invention, or fragments thereof, are in the pre-fusion conformation, i.e. they comprise (display) at least one epitope that is specific to the pre-fusion conformation F protein. An epitope that is specific to the pre-fusion conformation F protein is an epitope that is not presented in the post-fusion conformation. Without wishing to be bound by any particular theory, it is believed that the pre-fusion conformation of RSV F protein may contain epitopes that are the same as those on the RSV F protein expressed on natural RSV virions, and therefore may provide advantages for eliciting protective neutralizing antibodies.

In certain embodiments, the pre-fusion RSV F proteins of the invention, or fragments thereof, comprise at least one epitope that is recognized by a pre-fusion specific monoclonal antibody, comprising a heavy chain CDR1 region of SEQ ID NO: 1, a heavy chain CDR2 region of SEQ ID NO: 2, a heavy chain CDR3 region of SEQ ID NO: 3 and a light chain CDR1 region of SEQ ID NO: 4, a light chain CDR2 region of SEQ ID NO: 5, and a light chain CDR3 region of SEQ ID NO: 6 (hereafter referred to as CR9501) and/or a pre-fusion specific monoclonal antibody, comprising a heavy chain CDR1 region of SEQ ID NO: 7, a heavy chain CDR2 region of SEQ ID NO: 8, a heavy chain CDR3 region of SEQ ID NO: 9 and a light chain CDR1 region of SEQ ID NO: 10, a light chain CDR2 region of SEQ ID NO: 11, and a light chain CDR3 region of SEQ ID NO: 12 (referred to as CR9502). CR9501 and CR9502 comprise the heavy and light chain variable regions, and thus the binding specificities, of the antibodies 58C5 and 30D8, respectively, which have previously been shown to bind specifically to RSV F protein in its pre-fusion conformation and not to the post-fusion conformation (see WO2012/006596).

In certain embodiments, the recombinant pre-fusion RSV F proteins are trimeric.

As used throughout the present application nucleotide sequences are provided from 5' to 3' direction, and amino acid sequences from N-terminus to C-terminus, as custom in the art.

As indicated above, fragments of the pre-fusion RSV F protein are also encompassed by the present invention. The fragment may result from either or both of amino-terminal (e.g. by cleaving off the signal sequence) and carboxy-terminal deletions (e.g. by deleting the transmembrane region and/or cytoplasmic tail). The fragment may be chosen to comprise an immunologically active fragment of the F protein, i.e. a part that will give rise to an immune response in a subject. This can be easily determined using in silico, in vitro and/or in vivo methods, all routine to the skilled person.

In certain embodiments, the encoded proteins or fragments thereof according to the invention comprise a signal sequence, also referred to as leader sequence or signal peptide, corresponding to amino acids 1-26 of SEQ ID NO: 13. Signal sequences typically are short (e.g. 5-30 amino acids long) amino acid sequences present at the N-terminus of the majority of newly synthesized proteins that are destined towards the secretory pathway, and are typically cleaved by signal peptidase to generate a free signal peptide and a mature protein.

In certain embodiments, the proteins or fragments thereof according to the invention do not comprise a signal sequence.

In certain embodiments, the (fragments of the) pre-fusion RSV F proteins are soluble. In certain embodiments, the stable pre-fusion RSV F proteins or fragments thereof according to the invention comprise a truncated F1 domain, and comprise a heterologous trimerization domain linked to said truncated F1 domain. According to the invention, it was shown that by linking a heterologous trimerization domain to the C-terminal amino acid residue of a truncated F1 domain, combined with the stabilizing mutation(s), soluble RSV F proteins are provided that show high expression and that bind to pre-fusion-specific antibodies, indicating that the proteins are in the pre-fusion conformation. In addition, the RSV F proteins are stabilized in the pre-fusion conformation, i.e. even after processing of the proteins they still bind to the pre-fusion specific antibodies CR9501 and/or CR9502, indicating that the pre-fusion specific epitope is retained.

In certain embodiments, the RSV F proteins are multimers of trimeric RSV F proteins. Thus, in some embodiments, the RSV F proteins may comprise an assembly domain for higher order assemblies of trimers.

It is known that RSV exists as a single serotype having two antigenic subgroups: A and B. The amino acid sequences of the mature processed F proteins of the two groups are about 93% identical. As used throughout the present application, the amino acid positions are given in reference to the sequence of RSV F protein of subgroup A (SEQ ID NO: 13). As used in the present invention, the wording "the amino acid at position "x" of the RSV F protein thus means the amino acid corresponding to the amino acid at position "x" in the RSV F protein of SEQ ID NO: 13. Note that, in the numbering system used throughout this application 1 refers to the N-terminal amino acid of an immature F0 protein (SEQ ID NO: 13) When another RSV strain is used, the amino acid positions of the F protein are to be numbered with reference to the numbering of the F protein of SEQ ID NO: 13 by aligning the sequences of the other RSV strain with the F protein of SEQ ID NO: 13 with the insertion of gaps as needed. Sequence alignments can be done using methods well known in the art, e.g. by CLUSTALW, Bioedit or CLC Workbench.

In certain embodiments, the RSV strain is the RSV strain of SEQ ID NO: 20.

In certain embodiments, the RSV strain is an RSV B strain. In certain embodiments, the RSV strain is the RSV B strain of SEQ ID NO: 15.

An amino acid according to the invention can be any of the twenty naturally occurring (or 'standard' amino acids) or variants thereof, such as e.g. D-amino acids (the D-enantiomers of amino acids with a chiral center), or any variants that are not naturally found in proteins, such as e.g. norleucine. The standard amino acids can be divided into several groups based on their properties. Important factors are charge, hydrophilicity or hydrophobicity, size and functional groups. These properties are important for protein structure and protein-protein interactions. Some amino acids have special properties such as cysteine, that can form covalent disulfide bonds (or disulfide bridges) to other cysteine residues, proline that induces turns of the protein backbone, and glycine that is more flexible than other amino acids. Table 1 shows the abbreviations and properties of the standard amino acids.

It will be appreciated by a skilled person that the mutations can be made to the protein by routine molecular biology procedures. The mutations according to the invention preferably result in increased expression levels and/or increased stabilization of the pre-fusion RSV F proteins as compared RSV F proteins that do not comprise these mutation(s).

In certain embodiments, the pre-fusion RSV F proteins or fragments thereof comprise at least one further mutation selected from the group consisting of:
  (a) a mutation of the amino acid residue on position 67; and
  (b) a mutation of the amino acid residue on position 486.

In certain embodiments, the at least one further mutation is selected from the group consisting of:
  (a) a mutation of the amino acid residue N/T on position 67 into I; and
  (b) a mutation of the amino acid residue D on position 486 into N.

In certain embodiments, the pre-fusion RSV F proteins or fragments thereof comprise at least four mutations (as compared to a wild-type RV F protein, e.g. the comprising the amino acid sequence of SEQ ID NO: 13). In certain embodiments, the proteins or fragments thereof comprise at least five mutations.

In certain embodiments, the proteins or fragments thereof comprise at least six mutations.

In certain embodiments, the pre-fusion RSV F polypeptides thus comprise at least one further mutation selected from the group consisting of:
  (a) a mutation of the amino acid residue on position 46;
  (b) a mutation of the amino acid residue on position 83;
  (c) a mutation of the amino acid residue on position 92;
  (d) a mutation of the amino acid residue on position 184;
  (e) a mutation of the amino acid residue on position 203;
  (f) a mutation of the amino acid residue on position 207; and
  (g) a mutation of the amino acid residue on position 487.

In certain embodiments, the at least one further mutation is selected from the group consisting of:
  (a) a mutation of the amino acid residue S on position 46 into G;
  (b) a mutation of the amino acid residue L on position 83 into M:
  (c) a mutation of the amino acid residue E on position 92 into D;
  (d) a mutation of the amino acid residue G on position 184 into N;
  (e) a mutation of the amino acid residue L on position 203 into I;
  (f) a mutation of the amino acid residue V on position 207 into I: and
  (g) a mutation of the amino acid residue E on position 487 into Q, N or I.

In certain other embodiments, the heterologous trimerization domain comprises the amino acid sequence GYIPEAPRDGQAYVRKDGEWVLLSTFL (SEQ ID NO: 14).

As described above, in certain embodiments, the proteins of the invention or fragments thereof comprise a truncated F1 domain. As used herein a "truncated" F1 domain refers to a F1 domain that is not a full length F1 domain, i.e. wherein either N-terminally or C-terminally one or more amino acid residues have been deleted. According to the invention, at least the transmembrane domain and cytoplasmic tail have been deleted to permit expression as a soluble ectodomain.

In certain other embodiments, the trimerization domain is linked to amino acid residue 513 of the RSV F1 domain. In certain embodiments, the trimerization domain thus comprises SEQ ID NO: 14 and is linked to amino acid residue 513 of the RSV F1 domain.

In certain embodiments, the RSV F protein of the invention comprises the amino acid sequence of SEQ ID NO: 21.

In certain embodiments, the level of expression of the pre-fusion RSV F proteins of the invention is increased, as compared to a wild-type RSV F protein. In certain embodiments the level of expression is increased at least 5-fold, preferably up to 10-fold. In certain embodiments, the level of expression is increased more than 10-fold.

The pre-fusion RSV F proteins according to the invention are stable, i.e. do not readily change into the post-fusion conformation upon processing of the proteins, such as e.g. purification, freeze-thaw cycles, and/or storage etc.

In certain embodiments, the pre-fusion RSV F proteins according to the invention have an increased stability upon storage a 4° C. as compared to a RSV F protein without the mutation(s). In certain embodiments, the proteins are stable upon storage at 4° C. for at least 30 days, preferably at least 60 days, preferably at least 6 months, even more preferably at least 1 year. With "stable upon storage", it is meant that the proteins still display the at least one epitope specific for the a pre-fusion specific antibody (e.g. CR9501) upon storage of the protein in solution (e.g. culture medium) at 4° C. for at least 30 days. In certain embodiments, the proteins display the at least one pre-fusion specific epitope for at least 6 months, preferably for at least 1 year upon storage of the pre-fusion RSV F proteins at 4° C.

In certain embodiments, the pre-fusion RSV F proteins according to the invention have an increased stability when subjected to heat, as compared to RSV F proteins without said mutation(s). In certain embodiments, the pre-fusion REV F proteins are heat stable for at least 30 minutes at a temperature of 55° C., preferably at 58° C., more preferably at 60° C. With "heat stable" it is meant that the proteins still display the at least one pe-fusion specific epitope after having been subjected for at least 30 minutes to an increased temperature (i.e. a temperature of 55° C. or above), e.g. as determined using a method as described in the Examples (see FIG. 4).

In certain embodiments, the proteins display the at least one pre-fusion specific epitope after being subjected to 1 to 6 freeze-thaw cycles in an appropriate formulation buffer.

As used throughout the present application nucleotide sequences are provided from 5' to 3' direction, and amino acid sequences from N-terminus to C-terminus, as custom in the art.

In certain embodiments, the encoded proteins according to the invention further comprise a leader sequence, also referred to as signal sequence or signal peptide, corresponding to amino acids 1-26 of SEQ ID NO: 13. This is a short (typically 5-30 amino acids long) peptide present at the N-terminus of the majority of newly synthesized proteins that are destined towards the secretory pathway. In certain embodiments, the proteins according to the invention do not comprise a leader sequence.

In certain embodiments, the proteins comprise a HIS-Tag. A His-Tag or polyhistidine-tag is an amino acid motif in proteins that consists of at least five histidine (H) residues, often at the N- or C-terminus of the protein, which is generally used for purification purposes.

The present invention further provides nucleic acid molecules encoding the RSV F proteins according to the invention.

In preferred embodiments, the nucleic acid molecules encoding the proteins according to the invention are codon-optimized for expression in mammalian cells, preferably human cells. Methods of codon-optimization are known and have been described previously (e.g. WO 96/09378). A sequence is considered codon-optimized if at least one non-preferred codon as compared to a wild type sequence is replaced by a codon that is more preferred. Herein, a non-preferred codon is a codon that is used less frequently in an organism than another codon coding for the same amino acid, and a codon that is more preferred is a codon that is used more frequently in an organism than a non-preferred codon. The frequency of codon usage for a specific organism can be found in codon frequency tables, such as in website: www.kazusa.or.jp/codon. Preferably more than one non-preferred codon, preferably most or all non-preferred codons, are replaced by codons that are more preferred. Preferably the most frequently used codons in an organism are used in a codon-optimized sequence. Replacement by preferred codons generally leads to higher expression.

It will be understood by a skilled person that numerous different polynucleotides and nucleic acid molecules can encode the same protein as a result of the degeneracy of the genetic code. It is also understood that skilled persons may, using routine techniques, make nucleotide substitutions that do not affect the protein sequence encoded by the nucleic acid molecules to reflect the codon usage of any particular host organism in which the proteins are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may or may not include introns.

Nucleic acid sequences can be cloned using routine molecular biology techniques, or generated de novo by DNA synthesis, which can be performed using routine procedures by service companies having business in the field of DNA synthesis and/or molecular cloning (e.g. GeneArt, GenScripts, Invitrogen, Eurofins).

The invention also provides vectors comprising a nucleic acid molecule as described above. In certain embodiments, a nucleic acid molecule according to the invention thus is part of a vector. Such vectors can easily be manipulated by methods well known to the person skilled in the art, and can for instance be designed for being capable of replication in prokaryotic and/or eukaryotic cells. In addition, many vectors can be used for transformation of eukaryotic cells and will integrate in whole or in part into the genome of such cells, resulting in stable host cells comprising the desired nucleic acid in their genome. The vector used can be any vector that is suitable for cloning DNA and that can be used for transcription of a nucleic acid of interest. Suitable vectors according to the invention are e.g. adenovectors, alphavirus, paramyxovirus, vaccinia virus, herpes virus, retroviral vectors etc. The person skilled in the art is capable of choosing suitable expression vectors, and inserting the nucleic acid sequences of the invention in a functional manner.

Host cells comprising the nucleic acid molecules encoding the pre-fusion RSV F proteins form also part of the invention. The pre-fusion RSV F proteins may be produced through recombinant DNA technology involving expression of the molecules in host cells, e.g. Chinese hamster ovary (CHO) cells, tumor cell lines, BHK cells, human cell lines such as HEK293 cells, PER.C6 cells, or yeast, fungi, insect cells, and the like, or transgenic animals or plants. In certain embodiments, the cells are from a multicellular organism, in certain embodiments they are of vertebrate or invertebrate origin. In certain embodiments, the cells are mammalian cells. In certain embodiments, the cells are human cells. In general, the production of a recombinant proteins, such the pre-fusion RSV F proteins of the invention, in a host cell comprises the introduction of a heterologous nucleic acid molecule encoding the protein in expressible format into the host cell, culturing the cells under conditions conducive to expression of the nucleic acid molecule and allowing expression of the protein in said cell. The nucleic acid molecule encoding a protein in expressible format may be in the form of an expression cassette, and usually requires sequences capable of bringing about expression of the nucleic acid, such as enhancer(s), promoter, polyadenylation signal, and the like. The person skilled in the art is aware that various promoters can be used to obtain expression of a gene in host cells. Promoters can be constitutive or regulated, and can be obtained from various sources, including viruses, prokaryotic, or eukaryotic sources, or artificially designed.

Cell culture media are available from various vendors, and a suitable medium can be routinely chosen for a host cell to express the protein of interest, here the pre-fusion RSV F proteins. The suitable medium may or may not contain serum.

A "heterologous nucleic acid molecule" (also referred to herein as 'transgene') is a nucleic acid molecule that is not naturally present in the host cell. It is introduced into for instance a vector by standard molecular biology techniques. A transgene is generally operably linked to expression control sequences. This can for instance be done by placing the nucleic acid encoding the transgene(s) under the control of a promoter. Further regulatory sequences may be added. Many promoters can be used for expression of a transgene(s), and are known to the skilled person, e.g. these may comprise viral, mammalian, synthetic promoters, and the like. A non-limiting example of a suitable promoter for obtaining expression in eukaryotic cells is a CMV-promoter (U.S. Pat. No. 5,385,839), e.g. the CMV immediate early promoter, for instance comprising nt. −735 to +95 from the CMV immediate early gene enhancer/promoter. A polyadenylation signal, for example the bovine growth hormone polyA signal (U.S. Pat. No. 5,122,458), may be present behind the transgene(s). Alternatively, several widely used expression vectors are available in the art and from commercial sources, e.g. the pcDNA and pEF vector series of Invitrogen, pMSCV and pTK-Hyg from BD Sciences, pCMV-Script from Stratagene, etc, which can be used to recombinantly express the protein of interest, or to obtain suitable promoters and/or transcription terminator sequences, polyA sequences, and the like.

The cell culture can be any type of cell culture, including adherent cell culture, e.g. cells attached to the surface of a culture vessel or to microcarriers, as well as suspension culture. Most large-scale suspension cultures are operated as batch or fed-batch processes because they are the most straightforward to operate and scale up. Nowadays, continuous processes based on perfusion principles are becoming more common and are also suitable. Suitable culture media are also well known to the skilled person and can generally be obtained from commercial sources in large quantities, or custom-made according to standard protocols. Culturing can be done for instance in dishes, roller bottles or in bioreactors, using batch, fed-batch, continuous systems and the like. Suitable conditions for culturing cells are known (see e.g. Tissue Culture, Academic Press, Kruse and Paterson, editors (1973), and R. I. Freshney, Culture of animal cells: A manual of basic technique, fourth edition (Wiley-Liss Inc., 2000, ISBN 0-471-34889-9)).

The invention further provides compositions comprising a pre-fusion RSV F protein and/or a nucleic acid molecule, and/or a vector, as described above. The invention thus provides compositions comprising a pre-fusion RSV F protein that displays an epitope that is present in a pre-fusion conformation of the RSV F protein but is absent in the post-fusion conformation. The invention also provides compositions comprising a nucleic acid molecule and/or a vector, encoding such pre-fusion RSV F protein. The invention further provides immunogenic compositions comprising a pre-fusion RSV F protein, and/or a nucleic acid molecule, and/or a vector, as described above. The invention also provides the use of a stabilized pre-fusion RSV F protein, a nucleic acid molecule, and/or a vector, according to the invention, for inducing an immune response against RSV F protein in a subject. Further provided are methods for inducing an immune response against RSV F protein in a subject, comprising administering to the subject a pre-fusion RSV F protein, and/or a nucleic acid molecule, and/or a vector, according to the invention. Also provided are pre-fusion RSV F proteins, nucleic acid molecules, and/or vectors, according to the invention for use in inducing an immune response against RSV F protein in a subject. Further provided is the use of the pre-fusion RSV F proteins, and/or nucleic acid molecules, and/or vectors according to the invention for the manufacture of a medicament for use in inducing an immune response against RSV F protein in a subject.

The pre-fusion RSV F proteins, nucleic acid molecules, or vectors of the invention may be used for prevention (prophylaxis) and/or treatment of RSV infections. In certain embodiments, the prevention and/or treatment may be targeted at patient groups that are susceptible RSV infection. Such patient groups include, but are not limited to e.g., the elderly (e.g. ≥50 years old, ≥60 years old, and preferably ≥65 years old), the young (e.g. ≤5 years old, ≤1 year old), hospitalized patients and patients who have been treated with an antiviral compound but have shown an inadequate antiviral response.

The pre-fusion RSV F proteins, nucleic acid molecules and/or vectors according to the invention may be used e.g. in stand-alone treatment and/or prophylaxis of a disease or condition caused by RSV, or in combination with other prophylactic and/or therapeutic treatments, such as (existing or future) vaccines, antiviral agents and/or monoclonal antibodies.

The invention further provides methods for preventing and/or treating RSV infection in a subject utilizing the pre-fusion RSV F proteins, nucleic acid molecules and/or vectors according to the invention. In a specific embodiment, a method for preventing and/or treating RSV infection in a subject comprises administering to a subject in need thereof an effective amount of a pre-fusion RSV F protein, nucleic acid molecule and/or a vector, as described above. A therapeutically effective amount refers to an amount of a protein, nucleic acid molecule or vector, that is effective for preventing, ameliorating and/or treating a disease or condition resulting from infection by RSV. Prevention encompasses inhibiting or reducing the spread of RSV or inhibiting or reducing the onset, development or progression of one or more of the symptoms associated with infection by RSV. Amelioration as used in herein may refer to the reduction of visible or perceptible disease symptoms, viremia, or any other measurable manifestation of influenza infection.

For administering to subjects, such as humans, the invention may employ pharmaceutical compositions comprising a pre-fusion RSV F protein, a nucleic acid molecule and/or a vector as described herein, and a pharmaceutically acceptable carrier or excipient. In the present context, the term "pharmaceutically acceptable" means that the carrier or excipient, at the dosages and concentrations employed, will not cause any unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). The RSV F proteins, or nucleic acid molecules, preferably are formulated and administered as a sterile solution although it may also be possible to utilize lyophilized preparations. Sterile solutions are prepared by sterile filtration or by other methods known per se in the art. The solutions are then lyophilized or filled into pharmaceutical dosage containers. The pH of the solution generally is in the range of pH 3.0 to 9.5, e.g. pH 5.0 to 7.5. The RSV F proteins typically are in a solution having a suitable pharmaceutically acceptable buffer, and the composition may also contain a salt. Optionally stabilizing agent may be present, such as albumin. In certain embodiments, detergent is added. In certain embodiments, the RSV F proteins may be formulated into an injectable preparation.

In certain embodiments, a composition according to the invention further comprises one or more adjuvants. Adjuvants are known in the art to further increase the immune response to an applied antigenic determinant. The terms "adjuvant" and "immune stimulant" are used interchangeably herein, and are defined as one or more substances that cause stimulation of the immune system. In this context, an adjuvant is used to enhance an immune response to the RSV F proteins of the invention. Examples of suitable adjuvants include aluminium salts such as aluminium hydroxide and/or aluminium phosphate; oil-emulsion compositions (or oil-in-water compositions), including squalene-water emulsions, such as MF59 (see e.g. WO 90/14837); saponin formulations, such as for example QS21 and Immunostimulating Complexes (ISCOMS) (see e.g. U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as *E. coli* heat labile enterotoxin LT, cholera toxin CT, and the like; eukaryotic proteins (e.g. antibodies or fragments thereof (e.g. directed against the antigen itself or CD1a, CD3, CD7, CD80) and ligands to receptors (e.g. CD40L, GMCSF, GCSF, etc), which stimulate immune response upon interaction with recipient cells. In certain embodiments the compositions of the invention comprise aluminium as an adjuvant, e.g. in the form of aluminium hydroxide, aluminium phosphate, aluminium potassium phosphate, or combinations thereof, in concentrations of 0.05-5 mg, e.g. from 0.075-1.0 mg, of aluminium content per dose.

The pre-fusion RSV F proteins may also be administered in combination with or conjugated to nanoparticles, such as e.g. polymers, liposomes, virosomes, virus-like particles. The pre-fusion F proteins may be combined with, encapsidated in or conjugated to the nanoparticles with or without adjuvant. Encapsulation within liposomes is described, e.g. in U.S. Pat. No. 4,235,877. Conjugation to macromolecules is disclosed, for example in U.S. Pat. Nos.

4,372,945 or 4,474,757. In other embodiments, the RSV F proteins are assembled in higher order assemblies of multimers.

In other embodiments, the compositions do not comprise adjuvants.

In certain embodiments, the invention provides methods for making a vaccine against respiratory syncytial virus (RSV), comprising providing a composition according to the invention and formulating it into a pharmaceutically acceptable composition. The term "vaccine" refers to an agent or composition containing an active component effective to induce a certain degree of immunity in a subject against a certain pathogen or disease, which will result in at least a decrease (up to complete absence) of the severity, duration or other manifestation of symptoms associated with infection by the pathogen or the disease. In the present invention, the vaccine comprises an effective amount of a pre-fusion RSV F protein and/or a nucleic acid molecule encoding a pre-fusion RSV F protein, and/or a vector comprising said nucleic acid molecule, which results in an immune response against the F protein of RSV. This provides a method of preventing serious lower respiratory tract disease leading to hospitalization and the decrease in frequency of complications such as pneumonia and bronchiolitis due to RSV infection and replication in a subject. The term "vaccine" according to the invention implies that it is a pharmaceutical composition, and thus typically includes a pharmaceutically acceptable diluent, carrier or excipient. It may or may not comprise further active ingredients. In certain embodiments it may be a combination vaccine that further comprises other components that induce an immune response, e.g. against other proteins of RSV and/or against other infectious agents. The administration of further active components may for instance be done by separate administration or by administering combination products of the vaccines of the invention and the further active components.

Compositions may be administered to a subject, e.g. a human subject. The total dose of the RSV F proteins in a composition for a single administration can for instance be about 0.01 µg to about 10 mg, e.g. 1 µg-1 mg, e.g. 10 µg-100 µg. Determining the recommended dose will be carried out by experimentation and is routine for those skilled in the art.

Administration of the compositions according to the invention can be performed using standard routes of administration. Non-limiting embodiments include parenteral administration, such as intradermal, intramuscular, subcutaneous, transcutaneous, or mucosal administration, e.g. intranasal, oral, and the like. In one embodiment a composition is administered by intramuscular injection. The skilled person knows the various possibilities to administer a composition, e.g. a vaccine in order to induce an immune response to the antigen(s) in the vaccine.

A subject as used herein preferably is a mammal, for instance a rodent, e.g. a mouse, a cotton rat, or a non-human-primate, or a human. Preferably, the subject is a human subject.

The proteins, nucleic acid molecules, vectors, and/or compositions may also be administered, either as prime, or as boost, in a homologous or heterologous prime-boost regimen. If a boosting vaccination is performed, typically, such a boosting vaccination will be administered to the same subject at a time between one week and one year, preferably between two weeks and four months, after administering the composition to the subject for the first time (which is in such cases referred to as 'priming vaccination'). In certain embodiments, the administration comprises a prime and at least one booster administration.

In addition, the proteins of the invention may be used as diagnostic tool, for example to test the immune status of an individual by establishing whether there are antibodies in the serum of such individual capable of binding to the protein of the invention. The invention thus also relates to an in vitro diagnostic method for detecting the presence of an RSV infection in a patient said method comprising the steps of a) contacting a biological sample obtained from said patient with a protein according to the invention; and b) detecting the presence of antibody-protein complexes.

Stabilized pre-fusion RSV F proteins obtainable and/or obtained by such method also form part of the invention, as well as uses thereof as described above.

EXAMPLES

Example 1

Preparation of Stable Pre Fusion RSV F Polypeptide of SEQ ID NO: 21

To increase the stability of RSV F in the pre-fusion conformation two additional amino acid substitutions were introduced in a pre-fusion RSV F variant that was described previously (WO2014/174018 and WO2014/202570). The constructs were synthesized and codon-optimized at Gene Art (Life Technologies, Carlsbad, Calif.). The constructs were cloned into pCDNA2004 or generated by standard methods widely known within the field involving site-directed mutagenesis and PCR and sequenced. The expression platform used was the 293Freestyle cells (Life Technologies). The cells were transiently transfected using 293Fectin (Life Technologies) according to the manufacturer's instructions and cultured for 5 days at 37° C. and 10% $CO_2$. The culture supernatant was harvested and spun for 5 minutes at 300 g to remove cells and cellular debris. The spun supernatant was subsequently sterile filtered using a 0.22 um vacuum filter and stored at 4° C. until use.

Example 2

Purification of Pre-Fusion RSV F Protein

Figure 2:
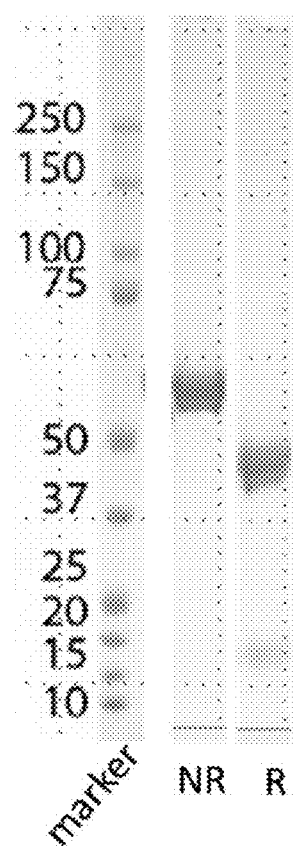
FIG. 2: A) SDS-PAGE analysis of the F N67I, S215P, T357K, N371Y, D486N protein sample containing peak from the SEC chromatogram under reducing (R) and non-reducing (NR). The gels are stained with Coomassie Brilliant Blue.

The recombinant polypeptide was purified by a 2-step purification protocol applying a cat-ion exchange column for the initial purification and subsequently a superdex200 column for the polishing step to remove residual contaminants. For the initial ion-exchange step the culture supernatant was diluted with 2 volumes of 50 mM NaOAc pH 5.0 and passed over a 5 ml HiTrap Capto S column at 5 ml per minute. Subsequently the column was washed with 10 column volumes (CV) of 20 mM NaOAc, 50 mM NaCl, 0.01% (v/v) tween20, pH 5 and eluted 2 CV of 20 mM NaOAc, 1M NaCl, 0.01% (v/v) tween20, pH 5. The eluate was concentrated using a spin concentrator and the protein was further purified using a superdex200 column using 40 mM Tris, 500 mM NaCl, 0.01% (v/v) tween20, pH 7.4 as running buffer. In FIG. 1 the chromatogram of the gel filtration column is shown. The dominant peak contained the pre-fusion RSV F protein. The fractions containing this peak were again pooled and the protein concentration was determined using OD280 and stored a 4° C. until use. In FIG. 2 a non-reduced and reduced SDS-PAGE analysis of the final protein preparation is shown and as can be seen the purity was >95%. The identity of the band was verified using western blotting and protein F specific antibodies (not shown).

Quantitative Octet (BioLayer Interferometry) was used for measuring protein concentration in the supernatants. CR9501 (an antibody specifically recognizing pre-fusion RSV F protein) and CR9503 (recognizing post-fusion RSV F protein) were biotinylated by standard protocols and immobilized on Streptavidin biosensors (ForteBio, Portsmouth, UK). Afterwards, the coated biosensors were blocked in mock cell culture supernatant. A quantitative experiment was performed as follows: temperature 30 C, shaking speed 1000 rpm, time of the assay 300 sec.

Figure 3:
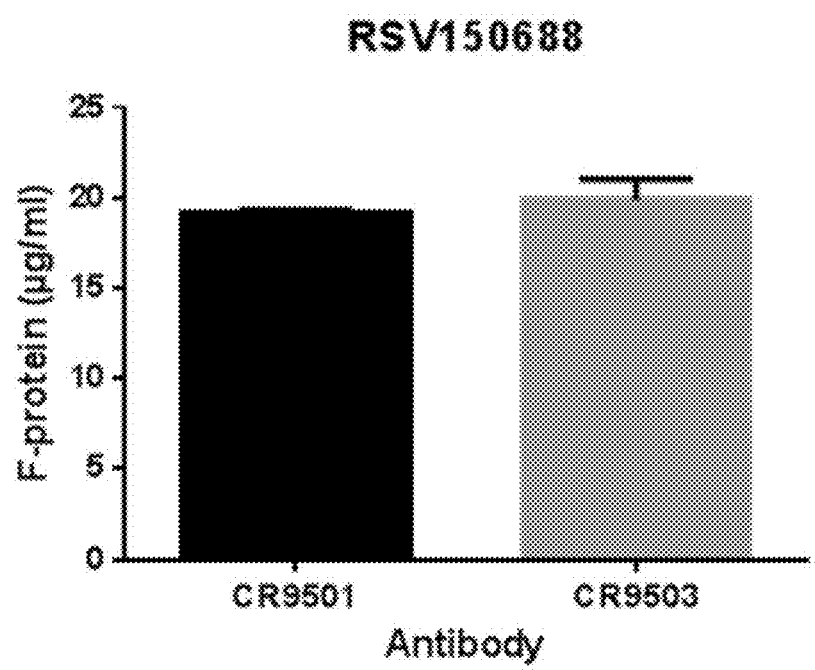
FIG. 3: The protein concentration of purified RSV F protein F N67I, S215P, T357K, N371Y, D486N was measured by Q Octet assay with CR9501 and CR9503 monoclonal antibodies. CR9501 only binds to RSV F in the pre-fusion conformation. CR9503 binds RSV F both in the pre-fusion conformation and the post-fusion conformation. Plotted as Mean±SE.

The concentration of the protein was calculated using a standard curve. The standard curve was prepared for each coated antibody using the pre-fusion RSV F protein (Krarup et. al., 2015, supra) diluted in mock medium (FIG. 3). The data analysis was done using the ForteBio Data Analysis 6.4 software (ForteBio).

Example 3

Temperature Stability of the RSV F Protein

Figure 4:
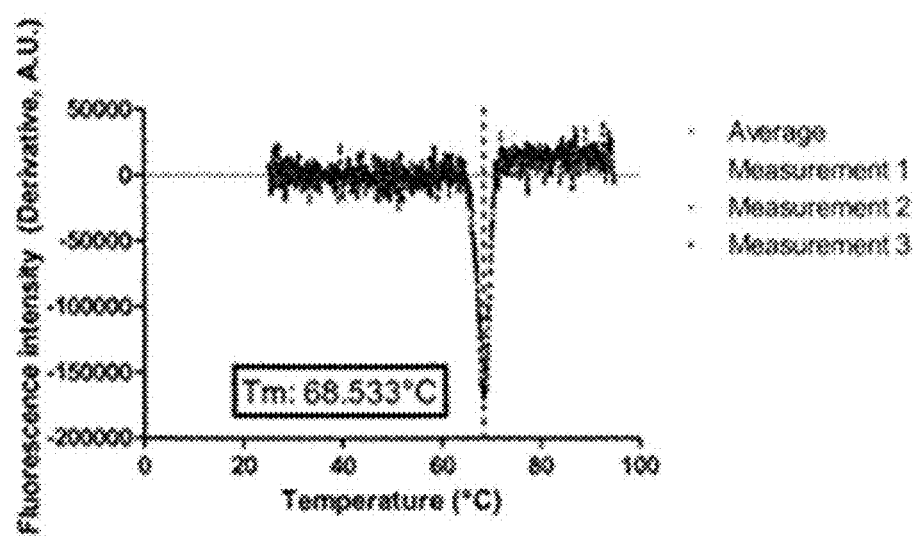
FIG. 4: Temperature stability of RSV F protein F N67I, S215P, T357K, N371Y, D486N. Melting temperature (Tm ° C.) determined by differential scanning fluorimetry (DSF) assay with SyproOrange fluorescent dye. Introduction of the T357K and N371Y substitutions increased the Tm of PRPM by 3.5 degrees to 68.5 degrees.

Temperature stability of the purified protein was determined by differential scanning fluorometry (DSF). The purified pre-fusion F protein was mixed with SYPRO orange fluorescent dye (Life Technologies S6650) in a 96-well optical qPCR plate. The optimal dye and protein concentration was determined experimentally (data not shown). Protein dilutions were performed in PBS, and a negative control sample containing the dye only was used as a reference subtraction. The measurement was performed in a qPCR instrument (Applied Biosystems ViiA 7) using the following parameters: a temperature ramp from 25-95° C. with a rate of 0.015° C. per second. Data was collected continuously. The melting curves were plotted using GraphPad PRISM software (version 5.04). Melting temperatures were calculated at the 50% maximum of fluorescence using a non-linear EC50 shift equation. The melting temperature of the RSV F protein of SEQ ID NO: 21 was 68.5 degrees (FIG. 4). A reference pre-fusion RSV F without substitutions at position 357 and 371 had a melting temperature of 65.0 which means the double mutation increased the melting temperature by 3.5 degrees.

TABLE 1

Standard amino acids, abbreviations and properties

| Amino Acid | 3-Letter | 1-Letter | Side chain polarity | Side chain charge (pH 7.4) |
|---|---|---|---|---|
| alanine | Ala | A | non-polar | Neutral |
| arginine | Arg | R | polar | Positive |
| asparagine | Asn | N | polar | Neutral |
| aspartic acid | Asp | D | polar | Negative |
| cysteine | Cys | C | non-polar | Neutral |
| glutamic acid | Glu | E | polar | Negative |
| glutamine | Gln | Q | polar | Neutral |
| glycine | Gly | G | non-polar | Neutral |
| histidine | His | H | polar | positive(10%) neutral(90%) |
| isoleucine | Ile | I | non-polar | Neutral |
| leucine | Leu | L | non-polar | Neutral |
| lysine | Lys | K | polar | Positive |
| methionine | Met | M | non-polar | Neutral |
| phenylalanine | Phe | F | non-polar | Neutral |
| proline | Pro | P | non-polar | Neutral |
| serine | Ser | S | polar | Neutral |
| threonine | Thr | T | polar | Neutral |
| tryptophan | Trp | W | non-polar | Neutral |
| tyrosine | Tyr | Y | polar | Neutral |
| valine | Val | V | non-polar | Neutral |

TABLE 2

Amino acid sequences of antibodies CR9501 and CR9502

| Ab | VH domain | VH CDR1 | VH CDR2 | VH CDR3 |
|---|---|---|---|---|
| CR9501 | Amino acids 1-125 of SEQ ID NO: 16 | GASINSDNYYWT (SEQ ID NO: 1) | HISYTGNTYYTPSLKS (SEQ ID NO: 2) | CGAYVLISNCGWFDS (SEQ ID NO: 3) |
| CR9502 | Amino acids 1-121 of SEQ ID NO:18 | GFTFSGHTIA (SEQ ID NO: 7) | WVSTNNGN-TEYAQKIQG (SEQ ID NO: 8) | EWLVMGGFAFDH (SEQ ID NO: 9) |
| CR9501 | Amino acids 1-107 of SEQ ID NO: 17 | QASQDISTYLN (SEQ ID NO: 4) | GASNLET (SEQ ID NO: 5) | QQYQYLPYT (SEQ ID NO: 6) |
| CR9502 | Amino acids 1-110 of SEQ ID NO: 19 | GANNIGSQNVH (SEQ ID NO: 10) | DDRDRPS (SEQ ID NO: 11) | QVWDSSRDQAVI (SEQ ID NO: 12) |

Sequences

RSV F protein full length sequence subgroup A (SEQ ID NO: 13)
MELLILKANAITTILTAVTFCFASGQNITEEFYQSTCSAVSKGYLSALRTGWYTSVITIE

LSNIKENKCNGTDAKVKLIKQELDKYKNAVTELQLLMQSTPATNNRARRELPRFMN

YTLNNAKKTNVTLSKKRKRRFLGFLLGVGSAIASGVAVSKVLHLEGEVNKIKSALLS

TNKAVVSLSNGVSVLTSKVLDLKNYIDKQLLPIVNKQSCSISNIETVIEFQQKNNRLLE

ITREFSVNAGVTTPVSTYMLTNSELLSLINDMPITNDQKKLMSNNVQIVRQQSYSIMSI

IKEEVLAYVVQLPLYGVIDTPCWKLHTSPLCTTNTKEGSNICLTRTDRGWYCDNAGS

VSFFPQAETCKVQSNRVFCDTMNSLTLPSEVNLCNVDIFNPKYDCKIMTSKTDVSSSV

ITSLGAIVSCYGKTKCTASNKNRGIIKTFSNGCDYVSNKGVDTVSVGNTLYYVNKQE

GKSLYVKGEPIINFYDPLVFPSDEFDASISQVNEKINQSLAFIRKSDELLHNVNAVKST

TNIMITTIIIVIIVILLSLIAVGLLLYCKARSTPVTLSKDQLSGINNIAFSN

RSV F protein B1 full length sequence (SEQ ID NO: 15)
MELLIHRLSAIFLTLAINALYLTSSQNITEEFYQSTCSAVSRGYFSALRTGWYTSVITIE

LSNIKETKCNGTDTKVKLIKQELDKYKNAVTELQLLMQNTPAANNRARREAPQYMN

YTINTTKNLNVSISKKRKRRFLGFLLGVGSAIASGIAVSKVLHLEGEVNKIKNALLSTN

KAVVSLSNGVSVLTSKVLDLKNYINNQLLPIVNQQSCRISNIETVIEFQQKNSRLLEIN

REFSVNAGVTTPLSTYMLTNSELLSLINDMPITNDQKKLMSSNVQIVRQQSYSIMSIIK

EEVLAYVVQLPIYGVIDTPCWKLHTSPLCTTNIKEGSNICLTRTDRGWYCDNAGSVSF

FPQADTCKVQSNRVFCDTMNSLTLPSEVSLCNTDIFNSKYDCKIMTSKTDISSSVITSL

GAIVSCYGKTKCTASNKNRGIIKTFSNGCDYVSNKGVDTVSVGNTLYYVNKLEGKN

LYVKGEPIINYYDPLVFPSDEFDASISQVNEKINQSLAFIRRSDELLHNVNTGKSTTNI

MITTIIIVIIVVLLSLIAIGLLLYCKAKNTPVTLSKDQLSGINNIAFSK

SEQ ID NO: 14 (fibritin)
GYIPEAPRDGQAYVRKDGEWVLLSTFL

RSV F protein CL57-v224 full length sequence (SEQ ID NO: 20)
MELPILKTNAITTILAAVTLCFASSQNITEEFYQSTCSAVSKGYLSALRTGWYTSVITIE

LSNIKENKCNGTDAKVKLIKQELDKYKNAVTELQLLMQSTPAANNRARRELPRFMN

YTLNNTKNNNVTLSKKRKRRFLGFLLGVGSAIASGIAVSKVLHLEGEVNKIKSALLST

NKAVVSLSNGVSVLTSKVLDLKNYIDKQLLPIVNKQSCSISNIETVIEFQQKNNRLLEI

TREFSVNAGVTTPVSTYMLTNSELLSLINDMPITNDQKKLMSNNVQIVRQQSYSIMSII

KEEVLAYVVQLPLYGVIDTPCWKLHTSPLCTTNTKEGSNICLTRTDRGWYCDNAGS

VSFFPQAETCKVQSNRVFCDTMNSLTLPSEVNLCNIDIFNPKYDCKIMTSKTDVSSSVI

TSLGAIVSCYGKTKCTASNKNRGIIKTFSNGCDYVSNKGVDTVSVGNTLYYVNKQEG

KSLYVKGEPIINFYDPLVFPSDEFDASISQVNEKINQSLAFIRKSDELLHNVNVGKSTT

NIMITTIIIVIIVILLLLIAVGLFLYCKARSTPVTLSKDQLSGINNIAFSN

RSV F, N67I, S215P, D486N, and 357K and 371Y (SEQ ID NO: 21)
MELLILKANAITTILTAVTFCFASGQNITEEFYQSTCSAVSKGYLSALRTGWYTSVITIE

LSNIKEIKCNGTDAKVKLIKQELDKYKNAVTELQLLMQSTPATNNRARRELPRFMNY

TLNNAKKTNVTLSKKRKRRFLGFLLGVGSAIASGVAVSKVLHLEGEVNKIKSALLST

NKAVVSLSNGVSVLTSKVLDLKNYIDKQLLPIVNKQSCSIPNIETVIEFQQKNNRLLEI

TREFSVNAGVTTPVSTYMLTNSELLSLINDMPITNDQKKLMSNNVQIVRQQSYSIMSII

KEEVLAYVVQLPLYGVIDTPCWKLHTSPLCTTNTKEGSNICLTRTDRGWYCDNAGS

VSFFPQAEKCKVQSNRVFCDTMYSLTLPSEVNLCNVDIFNPKYDCKIMTSKTDVSSS

Sequences-continued

VITSLGAIVSCYGKTKCTASNKNRGIIKTFSNGCDYVSNKGVDTVSVGNTLYYVNKQ

EGKSLYVKGEPIINFYDPLVFPSNEFDASISQVNEKINQSLAFIRKSDELLSAIGGYIPEA

PRDGQAYVRKDGEWVLLSTFL

CR9501 heavy chain (SEQ ID NO: 16):
QVQLVQSGPGLVKPSQTLALTCNVSGASINSDNYYWTWIRQRPGGGLEWIGHISYTG

NTYYTPSLKSRLSMSLETSQSQFSLRLTSVTAADSAVYFCAACGAYVLISNCGWFDS

WGQGTQVTVSSASTKGPSVFPLAPSSKSTSGGTAALGCLVKDYFPEPVTVSWNSGAL

TSGVHTFPAVLQSSGLYSLSSVVTVPSSSLGTQTYICNVNHKPSNTKVDKKVEPKSC

CR9501 light chain (SEQ ID NO: 17):
EIVMTQSPSSLSASIGDRVTITCQASQDISTYLNWYQQKPGQAPRLLIYGASNLETGVP

SRFTGSGYGTDFSVTISSLQPEDIATYYCQQYQYLPYTFAPGTKVEIKRTVAAPSVFIF

PPSDEQLKSGTASVVCLLNNFYPREAKVQWKVDNALQSGNSQESVTEQDSKDSTYS

LSSTLTLSKADYEKHKVYACEVTHQGLSSPVTKSFNRGEC

CR9502 heavy chain (SEQ ID NO: 18):
EVQLLQSGAELKKPGASVKISCKTSGFTFSGHTIAWVRQAPGQGLEWMGWVSTNNG

NTEYAQKIQGRVTMTMDTSTSTVYMELRSLTSDDTAVYFCAREWLVMGGFAFDHW

GQGTLLTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKRVEPKSC

CR9502 light chain (SEQ ID NO: 19):
QSVLTQASSVSVAPGQTARITCGANNIGSQNVHWYQQKPGQAPVLVVYDDRDRPSG

IPDRFSGSNSGNTATLTISRVEAGDEADYYCQVWDSSRDQAVIFGGGTKLTVLGQPK

AAPSVTLFPPSSEELQANKATLVCLISDFYPGAVTVAWKADSSPVKAGVETTTPSKQS

NNKYAASSYLSLTPEQWKSHRSYSCQVTHEGSTVEKTIAPTECS

---

The invention claimed is:

1. A recombinant pre-fusion respiratory syncytial virus (RSV) Fusion (F) protein comprising a mutation of the amino acid residue at position 215, a mutation of the amino acid residue at position 357, and a mutation of the amino acid residue at position 371, wherein the amino acid positions correspond to the numbering of the amino acid sequence of SEQ ID NO: 13.

2. The pre-fusion RSV F protein according to claim 1, comprising a mutation of the amino acid residue Ser at position 215 to Pro (S215P), a mutation of the amino acid residue Thr at position 357 to Lys (T357K) and a mutation of the amino acid residue Asn at position 371 to Tyr (N371Y).

3. The pre-fusion RSV F protein according to claim 1, further comprising at least one mutation selected from the group consisting of:
 a) a mutation of the amino acid residue at position 67; and
 b) a mutation of the amino acid residue at position 486.

4. The pre-fusion RSV F protein according to claim 3, wherein the at least one further mutation is selected from the group consisting of:
 c) a mutation of the amino acid residue Asn/Thr at position 67 to Ile; and
 d) a mutation of the amino acid residue Asp at position 486 to Asn.

5. The pre-fusion RSV F protein according to claim 1, wherein the protein comprises at least one epitope that is specific to the pre-fusion conformation F protein, wherein the at least one epitope is recognized by a pre-fusion specific monoclonal antibody, comprising a heavy chain CDR1 region of SEQ ID NO: 1, a heavy chain CDR2 region of SEQ ID NO: 2, a heavy chain CDR3 region of SEQ ID NO: 3 and a light chain CDR1 region of SEQ ID NO: 4, a light chain CDR2 region of SEQ ID NO: 5, and a light chain CDR3 region of SEQ ID NO: 6 and/or a pre-fusion specific monoclonal antibody, comprising a heavy chain CDR1 region of SEQ ID NO: 7, a heavy chain CDR2 region of SEQ ID NO: 8, a heavy chain CDR3 region of SEQ ID NO: 9 and a light chain CDR1 region of SEQ ID NO: 10, a light chain CDR2 region of SEQ ID NO: 67, and a light chain CDR3 region of SEQ ID NO: 11.

6. The pre-fusion RSV F protein according to claim 1, wherein the protein is trimeric.

7. The pre-fusion RSV F protein according to claim 1, comprising a truncated F1 domain and a heterologous trimerization domain linked to the truncated F1 domain.

8. The pre-fusion RSV F protein according to claim 7, wherein the heterologous trimerization domain comprises the amino acid sequence GYIPEAPRDGQAYVRKDGEWVLLSTFL (SEQ ID NO: 14).

9. The pre-fusion RSV F protein according to claim 7, wherein the trimerization domain is linked to amino acid residue 513 of the RSV F protein.

10. The pre-fusion RSV F protein according to claim 1, wherein the RSV F protein comprises the amino acid sequence of SEQ ID NO: 21.

11. A nucleic acid molecule encoding the pre-fusion RSV F protein according to claim 1.

12. The nucleic acid molecule according to claim 11, wherein the nucleic acid molecule has been codon-optimized for expression in mammalian cells.

13. A vector comprising the nucleic acid molecule according to claim 11.

14. A composition comprising a pre-fusion RSV F protein according to claim 1.

15. A method of inducing an immune response against RSV F protein in a subject in need thereof, the method comprising administering to the subject the pre-fusion RSV F protein according to claim 1.

16. A vaccine comprising the pre-fusion RSV F protein according to claim 1.

17. A method of prophylaxis and/or treatment of RSV infection in a subject in need thereof, the method comprising administering to the subject the pre-fusion RSV F protein according to claim 1.

18. A host cell comprising the nucleic acid molecule according to claim 11.

19. A method of preparing the pre-fusion RSV F protein according to claim 1, comprising growing a host cell comprising a nucleic acid molecule encoding the pre-fusion RSV F protein under conditions for expression of the pre-fusion RSV F protein.

20. A nucleic acid molecule encoding the pre-fusion RSV F protein according to claim 10.

21. A composition comprising a pre-fusion RSV F protein according to claim 10.

22. A composition comprising the nucleic acid molecule according to claim 11.

23. A composition comprising the nucleic acid molecule according to claim 20.

24. A method of inducing an immune response against RSV F protein in a subject in need thereof, the method comprising administering to the subject the pre-fusion RSV F protein according to claim 10.

25. A method of inducing an immune response against RSV F protein in a subject in need thereof, the method comprising administering to the subject the nucleic acid molecule according to claim 11.

26. A method of inducing an immune response against RSV F protein in a subject in need thereof, the method comprising administering to the subject the nucleic acid molecule according to claim 20.

27. A vaccine comprising the pre-fusion RSV F protein according to claim 10.

28. A vaccine comprising the nucleic acid molecule according to claim 11.

29. A vaccine comprising the nucleic acid molecule according to claim 20.

30. A method of prophylaxis and/or treatment of RSV infection in a subject in need thereof, the method comprising administering to the subject the pre-fusion RSV F protein according to claim 10.

31. A method of prophylaxis and/or treatment of RSV infection in a subject in need thereof, the method comprising administering to the subject the nucleic acid molecule according to claim 11.

32. A method of prophylaxis and/or treatment of RSV infection in a subject in need thereof, the method comprising administering to the subject the nucleic acid molecule according to claim 20.

* * * * *